United States Patent
Bahrmann et al.

(12)

(10) Patent No.: US 6,482,972 B1
(45) Date of Patent: *Nov. 19, 2002

(54) ISOMERIC NONANOLS AND DECANOLS, THEIR PREPARATION, PHTHALIC ESTERS OBTAINED THEREFROM AND THEIR USE AS PLASTICIZERS

(75) Inventors: Helmut Bahrmann, Hamminkeln (DE); Wilfried Fenske, Hamminkeln (DE); Wolfgang Greb, Dinslaken (DE); Peter Heymanns, Essen (DE); Peter Lappe, Dinslaken (DE); Thomas Müller, Dinslaken (DE); Jürgen Szameitat, Wesel (DE); Ernst Wiebus, Oberhausen (DE)

(73) Assignee: Hoechst Aktiengesellschaft (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/437,221

(22) Filed: May 8, 1995

Related U.S. Application Data

(63) Continuation of application No. 08/172,048, filed on Dec. 22, 1993, now abandoned.

(30) Foreign Application Priority Data

Dec. 22, 1992 (DE) .......................................... 42 43 524

(51) Int. Cl.$^7$ .............................................. C07C 69/76
(52) U.S. Cl. ........................... 560/76; 560/98; 568/863; 568/882; 568/883
(58) Field of Search ................................. 568/863, 882, 568/883; 560/98, 76

(56) References Cited

U.S. PATENT DOCUMENTS

| | | | | |
|---|---|---|---|---|
| 2,852,563 A | * | 9/1958 | Hagemeyer et al. | 260/601 |
| 4,426,542 A | * | 1/1984 | Barker et al. | 568/883 |
| 5,268,514 A | * | 12/1993 | Bahrmann et al. | 568/882 |

FOREIGN PATENT DOCUMENTS

| EP | 52999 | 6/1982 | ......... C07C/31/125 |
|---|---|---|---|
| EP | 0 052 999 A1 | * 6/1982 | |

OTHER PUBLICATIONS

Chemical Abstracts, vol. 115 No. 6; Aug. 12, 1991 Abstract # 51191P.

Chemical Abstracts, vol. 115 No. 6; Aug. 12, 1991 Abstract # 51190h.

* cited by examiner

*Primary Examiner*—Dwayne C. Jones
(74) *Attorney, Agent, or Firm*—Bierman, Muserlian and Lucas

(57) ABSTRACT

Mixtures of isomeric nonanols and decanols are obtained by joint aldol condensation of n-butanal and pentanals, and up to 1% by weight of 3-methylbutanal, hydrogenation of the aldol condensation product to the corresponding saturated alcohols, and separation from the reaction mixture of the components boiling at temperatures lower than those of the nonanols and decanols. The pentanals are mixtures of 60 to 90% by weight of n-pentanal and 10 to 40% by weight of 2-methylbutanal. The alcohol mixture is especially suitable for preparing ester plasticizers.

18 Claims, No Drawings

ISOMERIC NONANOLS AND DECANOLS, THEIR PREPARATION, PHTHALIC ESTERS OBTAINED THEREFROM AND THEIR USE AS PLASTICIZERS

This application is a continuation, of application Ser. No. 08/172,048, filed Dec. 22, 1993, now abandoned.

This Application claims the benefit of the priority of German Patent Application P 42 43 524.2, filed Dec. 22, 1992.

The invention relates to mixtures of isomeric nonanols and decanols, a process for their preparation, the phthalic esters obtained from these alcohols mixtures, and the use of these esters as plasticizers.

BACKGROUND OF THE INVENTION

Esters of phthalic acid have wide application as plasticizers, in particular for polyvinyl chloride. The alcohol components are principally primary alcohols having from 8 to 10 carbon atoms, the most important among them presently being 2-ethylhexanol. Phthalic esters of short-chain alcohols give plasticizers with good gelling powder; however, their higher volatility is a disadvantage. In comparison, long-chain esters gel more slowly but have poorer cold resistance.

The properties of the phthalic ester plasticizers are affected, not only by the size of the alcohol molecule, but also by the branching of the hydrocarbon chain. Thus, alcohols with little branching give ester plasticizers of high cold flexibility. Largely linear alcohols having from 9 to 10 carbon atoms in the molecule are therefore becoming increasingly important as alcohol components. A prerequisite for their use is that they are available in large quantities and at advantageous prices.

In German Patent 28 55 421, the plasticizers used are phthalates of $C_9$-alcohols, which are obtained by the oxo-reaction of $C_8$-olefins, hydrogenation of the reaction product, and esterification of the $C_9$-alcohols with phthalic anhydride. From 3% to 20% by weight of the starting olefins is said to have an isobutane skeleton in each molecular chain, less than 3% by weight of the olefins should contain quaternary carbon, and more than 90% by weight of the total amount of olefins is said to be present as n-octenes, monomethylheptenes, and dimethylhexenes. Furthermore, the weight ratio of the total amount of the n-octenes and monomethylheptenes to the dimethylhexenes is said to be more than 0.8.

Phthalic esters based on $C_{10}$-alcohols are the subject of the European Patent Application 3 66 089. The $C_{10}$-alcohols are used in the form of a mixture which is obtained by hydroformylation of a butene fraction, aldol condensation of the aldehyde mixture thus obtained, and subsequent hydrogenation. According to the process description, the hydroformylation step is not subject to any limitations. The catalysts used may be cobalt as well as rhodium; the addition of an organic compound of trivalent phosphorus is not excluded.

Another route to obtaining didecylphthalate mixtures is described in European Patent Application 4 24 767. The preparation of the esters is carried out in a multistage process by dimerization of butene mixtures, hydroformylation and hydrogenation of the resulting octene mixture to give a nonanol mixture, dehydration of the nonanol mixture to form a nonene mixture, and hydroformylation and hydrogenation of the nonene mixture to form the desired decanol mixture.

According to EP-B-52 999, plasticizer alcohols are prepared from a mixture of propylene and butenes in a molar ratio of 2:1 to 1:3. The olefins are jointly converted by the oxo reaction to a mixture of butyl and amyl aldehydes which is subjected to an aldol condensation. The resulting condensation products are subsequently hydrogenated to saturated alcohols.

The known alcohols or alcohol mixtures used for the preparation of plasticizers do not meet all the economic and technical requirements which are demanded of products produced on an industrial scale, because the starting materials are not available in sufficient quantity, the prices are too high, the conversion of the starting materials into the alcohols necessitates extremely costly processes, and/or the quality of the plasticizers prepared from the alcohols leaves much to be desired.

SUMMARY OF THE INVENTION

It is therefore an object of the present invention to develop suitable alcohol or alcohol mixtures for the preparation of high-quality plasticizers. They should be obtained from economically available raw materials in a technically simple manner.

This object is achieved by mixtures of isomeric nonanols and decanols which are obtained by joint aldol condensation of n-butanal and pentanals in a molar ratio of from 1:2 to 1:10. The pentanal mixtures comprise 60% to 90% by weight of n-pentanal, 10% to 40% by weight of 2-methylbutanal and up to 1% by weight of 3-methylbutanal. The aldol condensation product is then hydrogenated to form the saturated alcohols, and the components boiling at lower temperatures than the nonanols and decanols are removed from the reaction mixture.

It is preferable to use mixtures of isomeric nonanols and decanols which are prepared from n-butanal and pentanals which contain from 65% to 80% by weight of n-pentanal, 20% to 35% by eight of 2-methylbutanal, and up to 1% by weight of 3-methylbutanal. The alcohol mixtures are obtained by aldol condensation of a mixture containing n-butanal and pentanals in a molar ratio of 1:2 to 1:10, subsequent hydrogenation of the aldol condensation product, and removal of the 2-ethylhexanol formed. The source of the aldehydes is immaterial; the criteria are chiefly economic. To promote the formation of alcohols with little branching, the aldehydes must have the carbonyl group on the terminal carbon atom and, in the case of the pentanals, be at least substantially unbranched. Therefore, the pentanals used are mixtures containing from 60% to 90% by weight of n-pentanal, from 10 to 40% by weight of 2-methylbutanal, and up to 1% by weight of 3-methylbutanal.

Preferred starting materials are aldehydes prepared by hydroformylation (oxo process) of propylene or butenes. The required olefins are available in industrial quantities. Propylene is obtained as byproduct in ethylene production by pyrolysis of hydrocarbon mixtures in the presence of water vapor and also in some refinery processes, particularly the catalytic cracking of petroleum fractions.

Mixtures containing butene-1 and butene-2 are also necessarily obtained in considerable quantities as refinery byproducts in the production of automotive fuels and in the production of ethylene by thermal cracking of higher hydrocarbons. They are isolated from the $C_4$ cracking fractions of the pyrolysis product by extraction of the butadiene-1,3 by a selective solvent, and subsequent removal of the isobutene preferably by conversion into methyl t-butyl ether. Instead of extracting the butadiene-1,3, it can also be partly hydrogenated to butenes in the $C_4$ cracking fraction. The pyrolysis product freed of butadiene-1,3 is identified as raffinate I. If the isobutene has also been removed, it is referred to as raffinate II. This butene-1/butene-2 mixture is particularly suitable for further processing into decanols.

Basically, all current commercial hydroformylation processes are suitable for converting the olefins into aldehydes. Thus, the process can be carried out in the presence of cobalt or rhodium catalysts at pressures of 10 to 35 MPa and at temperatures of 120° to 180° C.; in the presence of cobalt/phosphine catalysts at pressures of from 5 to 10 MPa; or in the presence of rhodium catalysts which are modified by phosphine at temperatures of 60° to 150° C. and pressures of 1 to 8 MPa. In the last-described variant of the hydroformylation reaction, the catalyst may be homogeneously dissolved in—or form a separate phase from—the reaction mixture.

To prepare the aldehydes, propylene and the butenes may be reacted together, but preferably separately. It has proven particularly valuable to carry out the hydroformylation as a heterogeneous reaction in a two-phase system, a reaction which is described, for example, in DE-C-26 27 354. This embodiment of the oxo process ensures that olefins having their double bonds at a terminal carbon atom form largely n-aldehydes and that isomerization of the olefins by migration of the double bond during the reaction is essentially avoided.

The two-phase process is characterized by the presence of an organic phase, which contains the starting olefins and the reaction product, and an aqueous phase, in which the catalyst is dissolved. Catalysts used are water-soluble rhodium complexes which contain water-soluble phosphines as ligands. The phosphines include, in particular, triarylphosphines, trialkylphosphines, and arylated or alkylated diphosphines, the organic radicals of which are substituted by sulfonic acid groups or carboxyl groups. Their preparation is known and described, for example, in DE-PS 26 27 354 and DD-PS 259 194. The reaction of the olefins is carried out at temperatures of 70° to 150° C., preferably 100° to 130° C., and at pressures in the range of 0.4 to 30, in particular 1 to 10, MPa; the water gas used contains carbon monoxide and hydrogen in a volume ratio of 1:10 to 10:1. The rhodium concentration is 20 to 1000 ppm by weight, preferably 50 to 500 ppm by weight, based on the aqueous catalyst solution, with from 4 to 100 mol of water-soluble phosphine being used per mole of rhodium. The volume ratio of aqueous to organic phase is from 0.1 to 10:1.

The conversion of the butenes is appreciably increased if a phase-transfer reagent (solubilizer) is added to the aqueous catalyst solution. Materials which have proven particularly valuable are cationic solubilizers of the formula $[A-N(R^1R^2R^3)]^+E$, wherein A is a straight or branched chain alkyl radical having 6 to 25 carbon atoms; $R^1$, $R^2$, $R^3$ are individually straight or branched chain alkyl radicals having from 1 to 4 carbon atoms; and E is for example sulfate, tetrafluoroborate, acetate, methosulfate, benzenesulfonate, alkylbenzenesulfonate, toluenesulfonate, lactate, or citrate.

In the described process, as much as 99% of the propylene is converted, the butanal mixture obtained comprising over 95% by weight of the n-compound. When butene-1/butene-2 mixtures are used, the reaction with butene-1 is preferred. Depending on the reaction parameters selected, more than 95% of the butene-1 or butene-2 is converted. From 60% to 90% by weight of n-pentanal is formed, the remainder comprising 2-methylbutanol with or without 3-methylbutanal.

After completion of the separate or joint hydroformylation, the aldehydes are separated from the catalyst, from the unreacted reaction components, and from the other reaction products. In the case of the heterogeneous reaction, this is by simple phase seperation. For reaction in the homogeneous phase, a usual separation process such as distillation suffices.

In the subsequent aldol condensation, mixtures are used which contain, per mole of n-butanal, 2 to 10 mol, in particular 7 to 10 mol, of pentanals. The reaction of the aldehyde mixture is carried out in the conventional way using basic catalysts. Pretreatment of the aldehydes, for example a special purification, is not necessary. It is, however, advisable in the case of the butanals to remove i-butanal from the $C_4$-aldehyde mixture by distillation, if the proportion thereof in the mixture exceeds approximately 2% by weight. Suitable catalysts are alkali metal carbonates or alkali metal hydroxides, in particular compounds of sodium or potassium and amines, preferably tertiary amines, such as triethylamine, tri-n-propylamine and tri-n-butylamine. The reaction is carried out at temperatures of 60° to 160° C., in particular 80° to 130° C., and at atmospheric pressure or at a superatmospheric pressure of up to 1 MPa. The reaction time is from a few minutes to several hours and is, in particular, dependent on the catalyst type and reaction temperature. Because of their higher reactivity, the straight-chain aldehydes react preferentially. Self-condensation of n-butanal or n-pentanal forms $C_8$ or $C_{10}$-enals and the mixed condensation of n-butanal and n-pentanal gives $C_9$-enals. The reactions between n-butanal or n-pentanal and branched-chain pentanals proceed at appreciably lower rates; the reaction between branched-chain pentanals is largely insignificant.

The mixture of unsaturated aldehydes obtained by condensation is subsequently hydrogenated to a mixture containing nonyl and decyl alcohols together with 2-ethylhexanol and any butanols and pentanols arising from $C_4$- and $C_5$-aldehydes which may not have been converted by the aldol condensation. The addition of hydrogen is carried out in a known manner in the presence of catalysts. Suitable catalysts are, for example, hydrogenation catalysts based on nickel, chromium or copper. The hydrogenation temperature is usually between 100° and 180° C. and the pressure is 1 to 10 MPa. According to the invention, the alcohol mixture obtained is subjected to distillation at 100° to 125° C. and a pressure of 1 to 4 kPa (from 10 to 40 mbar) to remove 2-ethylhexanol, other alcohols, and impurities which boil at lower temperatures than the nonanols and decanols.

The remaining mixture of nonanols and decanols is especially suitable as the alcohol component in phthalic esters which are to be used as plasticizers. The preparation of phthalic esters is known [cf. Ullmann, Encyclopadie der Technischen Chemie (1979), Vol. 18, page 536 ff]. Phthalic anhydride is advantageously reacted with the nonanol/decanol mixture in a molar ratio of 1:2 to 1:3 in a single stage. The reaction rate can be increased by catalysts and/or by increasing the reaction temperature. To shift the equilibrium in the direction of ester formation, it is necessary to remove the water of reaction from the reaction mixture.

The phthalates obtained from the nonanol/decanol mixture of the invention are remarkable for their low volatility and good gelling ability.

EXAMPLE 1

980.0 g of 2.5% NaOH (0.61 mol) is heated to 60° C. under nitrogen, and a mixture of 272.8 g (3.17 mol) of n-valeraldehyde, 181.8 g (2.11 mol) of 2-methylbutanal, and 45.5 g (0.63 mol) of n-butyraldehyde is added over a period of 20 minutes. The mixture is then heated to 88° to 90° C. under reflux for one hour. After cooling to 30° C. the organic and aqueous phases separate.

The aldol condensation product is hydrogenated in the presence of a nickel catalyst at a pressure of 10 MPa and 140° C. After filtering out the catalyst, a crude alcohol mixture is obtained which has the following composition (% by weight) determined by gas chromatography:

| First fraction | 0.2 |
| 2-methylbutanol | 30.2 |
| n-pentanol | 0.3 |
| 2-ethylhexanol | 1.6 |
| 2-ethyl-4-methylhexanol | 2.1 |
| 2-propylhexanol | 6.4 |
| 2-ethylheptanol | 6.2 |
| 2-propyl-4-methylhexanol | 14.7 |
| 2-propylheptanol | 35.4 |
| Final fraction | 2.9 |

The distillative removal of the pentanols and 2-ethylhexanol gives an alcohol mixture with the following composition (% by weight):

| 2-ethyl-4-methylhexanol | 3.2 |
| 2-propylhexanol | 9.9 |
| 2-ethylheptanol | 9.6 |
| 2-propyl-4-methylhexanol | 22.6 |
| 2-propylheptanol | 54.7 |

The esterification with phthalic anhydride is carried out in the presence of sulfuric acid as the catalyst and cyclohexane for the azeotropic removal of the water of reaction. Neutralization, alcohol removal, and drying result in a mixture of phthalic esters of isomeric nonanols and decanols which has a density of 0.967 g/ml at 20° C. and a viscosity of 138 mPa.s.

EXAMPLE 2

980.0 g of 2.5% NaOH (0.61 mol) is heated to 60° C. under nitrogen and a mixture of 214.3 g (2.49 mol) of n-valeraldehyde, 143.0 g (1.66 mol) of 2-methylbutanal, and 142.8 g (1.98 mol) of n-butyraldehyde, is added dropwise over a period of 20 minutes. The mixture is heated to 89° to 92° C. under reflux for one hour. After cooling to 30° C., the organic and aqueous phases separate.

Hydrogenation as in Example 1 of the condensation product gives a crude alcohol mixture with the following composition (% by weight) determined by gas chromatography:

| First fraction | 0.2 |
| 2-methylbutanol | 20.9 |
| n-pentanol | 0.2 |
| 2-ethylhexanol | 10.9 |
| 2-ethyl-4-methylhexanol | 5.2 |
| 2-propylhexanol | 13.9 |
| 2-ethylheptanol | 13.5 |
| 2-propyl-4-methylhexanol | 10.0 |
| 2-propylheptanol | 22.3 |
| Final fraction | 2.9 |

The distillative removal of the pentanols and 2-ethylhexanol gives an alcohol mixture with the following composition (% by weight):

| 2-ethyl-4-methylhexanol | 8.0 |
| 2-propylhexanol | 21.4 |
| 2-ethylheptanol | 20.8 |
| 2-propyl-4-methylhexanol | 15.4 |
| 2-propylheptanol | 34.4 |

Esterification with phthalic anhydride as in Example 1 results in an ester mixture which has a viscosity of 118 mPa.s and a density of 0.969 g/ml.

EXAMPLE 3

A mixture of 280 g (3.25 mol) of n-valeraldehyde, 120.0 g (1.39 mol) of 2-methylbutanal, and 120.0 g (1.66 mol) of n-butyraldehyde is converted to aldols in the presence of 1016 g of 2.5% NaOH (0.63 mol) as in Example 1.

Hydrogenation as in Example 1 of the condensation product gives a crude alcohol mixture with the following composition (% by weight):

| First fraction | 0.7 |
| 2-methylbutanol | 17.9 |
| n-pentanol | 0.3 |
| 2-ethylhexanol | 7.0 |
| 2 ethyl-4-methylhexanol | 3.6 |
| 2-propylhexanol | 13.8 |
| 2-ethylheptanol | 13.5 |
| 2-propyl-4-methylhexanol | 9.5 |
| 2-propylheptanol | 31.7 |
| Final fraction | 2.0 |

The distillation workup gives an alcohol mixture with the following composition (% by weight):

| 2-ethyl-4-methylhexanol | 5.1 |
| 2-propylhexanol | 19.2 |
| 2-ethylheptanol | 18.7 |
| 2-propyl-4-methylhexanol | 13.1 |
| 2-propylheptanol | 43.9 |

Esterification with phthalic anhydride as in Example 1 results in an ester mixture which has a viscosity of 123 mpa.s and a density of 0.969 g/ml.

EXAMPLES 4 TO 7

The Examples 4 to 7 are carried out in the same manner as Example 1; the data relating to the composition of the starting mixture, the crude alcohol mixture, and the alcohol mixture suitable for plasticizer production are shown in the following Table.

| | Ex. 4 | Ex. 5 | Ex. 6 | Ex. 7 |
|---|---|---|---|---|
| Starting mixture n-valoraldehyde | | | | |
| (g) | 156.7 | 208.9 | 139.3 | 234.8 |
| (mol) | 1.82 | 2.43 | 1.62 | 2.73 |

-continued

|  | Ex. 4 | Ex. 5 | Ex. 6 | Ex. 7 |
|---|---|---|---|---|
| 2-methylbutanol |  |  |  |  |
| (g) | 17.4 | 52.0 | 34.8 | 26.1 |
| (mol) | 0.20 | 0.60 | 0.40 | 0.30 |
| n-butyraldehyde |  |  |  |  |
| (g) | 74.3 | 22.3 | 74.3 | 22.3 |
| (mol) | 1.03 | 0.31 | 1.03 | 0.31 |
| 2.5% strength NaOH |  |  |  |  |
| (g) | 480.5 | 528.0 | 480.0 | 528.5 |
| (mol) | 0.30 | 0.33 | 0.30 | 0.33 |
| Crude alcohol mixture (in % by weight) |  |  |  |  |
| First fraction | 0.2 | 0.2 | 0.2 | 0.2 |
| 2-methylbutanol | 4.6 | 13.1 | 9.9 | 6.5 |
| n-pentanol | 0.3 | 0.3 | 0.2 | 0.3 |
| 2-ethylhexanol | 10.2 | 0.9 | 10.9 | 0.9 |
| 2-ethyl-4-methylhexanol | 1.1 | 0.9 | 2.8 | 0.5 |
| 2-propylhexanol | 19.0 | 6.6 | 17.6 | 7.0 |
| 2-ethylheptanol | 18.5 | 6.4 | 16.9 | 6.7 |
| 2-propyl-4-methylhexanol | 3.3 | 10.1 | 6.2 | 6.1 |
| 2-propylheptanol | 40.6 | 59.6 | 33.2 | 69.8 |
| Final fraction | 1.9 | 1.9 | 2.1 | 2.0 |
| Alcohol mixture for plasticizer (in % by weight): |  |  |  |  |
| 2-ethyl-4-methylhexanol | 1.8 | 1.0 | 3.6 | 0.6 |
| 2-propylhexanol | 22.9 | 7.9 | 23.0 | 7.8 |
| 2-ethylheptanol | 22.3 | 7.6 | 22.0 | 7.4 |
| 2-propyl-methylhexanol | 4.0 | 12.1 | 8.2 | 6.8 |
| 2-propylheptanol | 49.0 | 71.4 | 43.2 | 77.4 |

The excellent gelling ability of the phthalic ester plasticizers produced from the alcohol mixture of the invention is shown by comparison with the established di(isodecyl)phthalate (DIDP) plasticizers.

While only a limited number of specific embodiments of the present invention have been expressly disclosed, it is, nonetheless, to be broadly construed and not to be limited except by the character of the claims appended hereto.

We claim:

1. A mixture consisting of isomeric nonanols and decanols which is the product of a joint aldol condensation of n-butanal and pentanals in a molar ratio of 1:2 to 1:1
   wherein said pentanals comprise 60% to 90% by weight of n-pentanal, 10% to 40% by weight of 2-methyl butanal, and up to 1% by weight of 3-methyl butanal, to form an aldol condensation product,
   hydrogenation of the said condensation product to form said isomeric nonanols and decanols, and separation therefrom of components having boiling points below those of said nonanols and decanols.

2. The mixture of claim 1 wherein said pentanals comprise 65% to 80% by weight of n-pentanal, 20% to 35% by weight of 2-methylbutanal, and up to 1% by weight of 3-methylbutanal.

3. A process for preparation of a mixture consisting isomeric nonanols and decanols wherein the propylene and butenes are hydroformylated separately to form mixtures of butanals and pentanals, joint condensation of said mixtures in the presence of at least one basic catalyst to form a condensation product,
   hydrogenation of said condensation product to form said mixture of said nonanols and decanols, and separation from said nonanols and decanols of components having boiling points below those of said nonanols and decanols.

4. The process of claim 3 wherein said catalyst comprises rhodium-phosphine complexes.

5. The process of claim 4 wherein said hydroformylation is carried out at 70° to 150° C. and under a pressure of 0.4 to 30 MPa.

6. The process of claim 3 wherein said condensation is at 60° to 160° C. in the presence of at least one tertiary amine.

7. The process of claim 3 wherein said hydrogenation is in the presence of at least one nickel catalyst at 100° to 180° C. under pressure of 1 to 10 MPa.

8. The process of claim 3 wherein said separation is by distillation.

9. The process of claim 8 wherein said distillation is at 100° to 125° C. under a pressure of 1 to 4 kPa.

10. A plasticizer which is the reaction product of the mixture of claim 1 with phthalic acid and/or phthalic anhydride.

11. The plasticizer of claim 10 wherein said pentanals comprise 65% to 80% by weight of n-pentanal, 20% to 35% by weight of 2-methylbutanal, and up to 1% by weight of 3-methylbutanal.

12. The process of claim 3 wherein said mixture is esterified with phthalic acid and/or phthalic anhydride.

13. The process of claim 12 wherein said catalyst comprises rhodium-phosphine complexes.

14. The process of claim 13 wherein said hydroformylation is carried out at 70° to 150° C. and under a pressure of 0.4 to 30 MPa.

15. The process of claim 12 wherein said condensation is at 60° to 160° C. in the presence of at least one tertiary amine.

16. The process of claim 12 wherein said hydrogenation is in the presence of at least one nickel catalyst at 100° to 180° C. under pressure of 1 to 10 MPa.

17. The process of claim 12 wherein said separation is by distillation.

18. The process of claim 17 wherein said distillation is at 100° to 125° C. under a pressure of 1 to 4 kPa.

* * * * *